United States Patent [19]
Giaroni et al.

[11] Patent Number: 6,162,841
[45] Date of Patent: Dec. 19, 2000

[54] BETAKETOSULPHONES DERIVATIVES SUITABLE TO THE USE AS POLYMERIZATION PHOTOINITIATORS AND PHOTOPOLYMERIZABLE SYSTEMS CONTAINING THE SAME

[75] Inventors: Paola Giaroni, Varese; Piero Di Battista, Peschiera Borromeo; Giuseppe Li Bassi, Gavirate, all of Italy

[73] Assignee: Lamberti S.p.A., Varese, Italy

[21] Appl. No.: 09/033,808

[22] PCT Filed: Sep. 11, 1995

[86] PCT No.: PCT/EP95/03567

§ 371 Date: Mar. 3, 1998

§ 102(e) Date: Mar. 3, 1998

[87] PCT Pub. No.: WO97/10270

PCT Pub. Date: Mar. 20, 1997

[51] Int. Cl.[7] ............... C08F 2/50; C08F 4/00; C08K 3/22; C09D 11/10
[52] U.S. Cl. ............... 522/36; 522/16; 522/17; 522/26; 522/27; 522/53; 522/55; 522/59; 522/75; 522/81; 522/83; 522/92; 522/96; 522/182
[58] Field of Search ............... 522/16, 17, 26, 522/27, 36, 59, 55, 53, 92, 96, 75, 83, 81, 182; 523/160

[56] References Cited

U.S. PATENT DOCUMENTS

| | | | |
|---|---|---|---|
| 3,903,322 | 9/1975 | Ravve et al. | 427/519 |
| 4,318,791 | 3/1982 | Felder et al. | |
| 4,374,984 | 2/1983 | Eichler et al. | 544/80 |
| 4,434,035 | 2/1984 | Eichler et al. | |
| 4,582,862 | 4/1986 | Berner et al. | 522/14 |
| 5,026,740 | 6/1991 | Li Bassi et al. | 522/14 |

OTHER PUBLICATIONS

AN 83–760394 WPINDEX Abstract of EP 88050A Sep. 25, 1993.

*Primary Examiner*—Susan W. Berman
*Attorney, Agent, or Firm*—Hedman, Gibson & Costigan, P.C.

[57] ABSTRACT

New betaketosulfonic derivatives, the process for their preparation, the photopolymerizable systems containing the same and their application as polymerization photoinitiators for inks, and particularly for inks having high content of pigments are described.

5 Claims, No Drawings

BETAKETOSULPHONES DERIVATIVES SUITABLE TO THE USE AS POLYMERIZATION PHOTOINITIATORS AND PHOTOPOLYMERIZABLE SYSTEMS CONTAINING THE SAME

FIELD OF THE INVENTION

The present invention concerns new betaketosulphones suitable to the use as polymerization photoinitiators, the process for their preparation and the photopolymerizable systems containing the same.

Said systems find application in the inks field and particularly in the field of the inks having high content in pigments.

PRIOR ART

The photochemical polymerization of monomers and unsaturated prepolymers is a widespread technique used in various technological fields, such as those of paints and lacquers, of printing inks, in the making of printing plates and electronic circuits, stencils for ceramics and textile printing, and in the manufacture of dental apparatuses.

In particular, in the production of printing inks, the photocross-linkable systems used are based on active monomers, such as derivatives of the acrylic and methacrylic acid, N-vinylpyrrolidone, vinyl ethers, styrene, allyl derivatives, maleic and fumaric acid derivatives; on ethylenic unsaturated polyester, polyether, polyurethane, silicone, epoxy oligomers and polymers; on pigments, fillers, additives, various auxiliares, on a photoinitiator or on a system composed of a mixture of photoinitiators, some of them particularly suitable to the pigmented system and other acting as adjuvants (benzophenone, benzyldimethylketale etc.). The constituent parts of these systems of photoinitiators are generally:

a) a photoinitiator at least, which must show an absorption spectrum in the spectral region where resins and pigments have a minimum in absorpion or reflection of the incident light (optical window) and where the light source used for the process emits a peak or a radiation band (light).

For the photoinitiator systems at present in use, this region is located between 360 and 420 nm.

b) a coinitiator at least, generally a tertiary amine with hydrogen atoms available on carbon in alpha position with respect to nitrogen, which is essential when the photoinitiator acts by a hydrogen extraction mechanism, such as benzophenone and thioxanthones.

Said coinitiator in any case turns out to be very useful even in the case of photoinitiators acting by homolytic breaking: in fact the tertiary amines eliminate the oxygen inhibitory effect, increasing the speed of the whole photopolymerization process.

The polymerization inhibition owing to oxygen is a problem particularly important for printing inks, considering their limited thickness and their high surface/volume ratio.

For such purposes aromatic aliphatic or entirely aliphatic amines are generally used, such as for instance triethylamine, N-methyldiethanolamine, N,N-dimethylethanolamine, p-dimethylaminoethylbenzoate, as is for instance described in the U.S. Pat. No. 4,318,791.

The photopolymerization of pigmented printing inks has always shown various technical problems connected to the existence of some necessities:

attainment of drying rates lying in the 15–200 m/min. range, compatible with the industrial application in printing and graphic arts;

achievement of a perfectly cross-linked film, avoiding the variation of the tone of the pigments added to the system, such as an undesired yellowing of the obtained film;

perfect covering of the support, to obtain which a high pigmentation is needed, about 20–60% by weight;

safety in the working environment limiting the residual odour, due to photolysis products or to not reacted monomers, particularly to acrylates, and limiting the presence of volatile substances during the photopolymerization stages.

Among the photoinitiators which have found grater use in the ink field there is the isopropyl thioxanthone (ITX), having the following formula

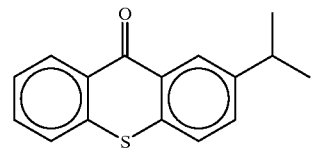

and similar derivatives (for instance the diethyl thioxanthone), as described in the American U.S. Pat. No. 4,434,035.

However the compound has the drawback to be coloured and consequently to give an undesired colouring to the white or light tone inks. Some attempts to correct such defects have been carried out, as described in the European Patent EP 88050, with the introduction of the photoinitiators belonging to the class of the aminoketones, among which the 2-methyl-1-[4-(methylthio)phenyl]-2-morpholino-1-propanone (MMMP) has been developed.

In this case the yellowing of the film turns out to be very low, but a serious limitation is presented by the residual odour due to the photolysis by-products of the photoinitiator after the irradiation process. Such odour is the cause of drawbacks during the productions in the working environment and persists in the processed goods; therefore the use of this product cannot be enlarged to the printing of the packagings destined to the food industry.

The introduction of such products on the market has been therefore limited and at the present time the coexistence of ITX and MMMP is noticed.

Recently the Applicant himself discovered a new family of photoinitiators of betaketosulfonic kind, described in the patent U.S. Pat. No. 5,026,740.

Some of the products belonging to such a class point out spectral requirements and reactivity suitable to the cross-linking of pigmented inks. The use of such compounds allow to obtain inks with a low yellowing degree, whether immediately after the exposure to the light sources, or by aging in the natural light; however the residual odour, even though not so marked as the previously cited cases, is a limit to their employment. Therefore the necessity is felt to find some products using which such residual odour after the photocross-linking is totally removed or remarkably reduced.

Within the limits of the family of photoinitiators just described, some structures have been surprisingly discovered showing photoinitiating properties, without generation of residual odour after the irradiation process, or generation of anomalous colouring or variation of tone of the film.

SUMMARY OF THE INVENTION

The present invention concerns photopolymerizable systems containing at least one betaketosulphone selected from the compounds having formula I:

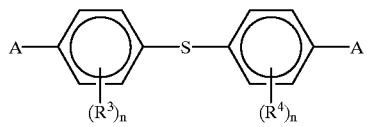

wherein A is

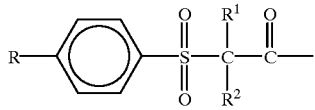

and II:

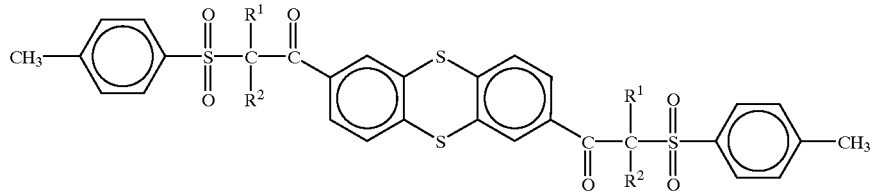

wherein

R, $R^1$, $R^2$, $R^3$, $R^4$ each independently are H or $C_{1-4}$ linear or branched alkyl chain and n is 0 or 1 particularly when said systems are pigmented inks.

Example of formula (I) is represented by the 4-4'-bis[2(4-methylphenylsulfonyl)-2-methyl-1-propanoyl]diphenyl sulfide, while an example of formula (II) corresponds to the 2,2-bis[2(4-methylphenylsulfonyl)-2-methyl-1-propanoyl]thianthrene.

The invention concerns, besides the compounds (I) and (II), the process for their preparation.

DETAILED DESCRIPTION OF THE INVENTION

According to the present invention, the compounds having formula (I) and (II) are used as photoinitiators in photopolymerizable systems, containing reactive monomers and oligomers. The word "photopolymerizable system" means in the present text a mixture of photopolymerizable or cross-linkable monomers and oligomers, at least one photoinitiator, fillers, pigments, dispersants and other additives of general use. The expression "photopolymerization" is meant in broad sense and includes, for instance, also the further polymerization or cross-linking of polymeric material, for instance of prepolymers, the homopolymerization, and the copolymerization of simple monomers, and the combination of these kinds of reaction. The monomers suitable for the system of the present invention comprise the esters of the acrylic and methacrylic acid with aliphatic alcohols, glycols, polyhydroxylated compounds such as pentaerythritol or trimethylolpropane or aminoalcohols; acrylonitrile; acrylamide and their derivatives; esters of vinyl alcohol with aliphatic or acrylic acids; vinyl ethers; N-vinylpyrrolidone; mono and polyfunctional allyl ethers such as the trimethylolpropandiallyl ether; styrene and alpha-methylstyrene; derivatives of maleic and fumaric acids.

The reactive oligomers suitable for the present invention include polyesters, polyacrylates, polyurethanes, epoxy resins, polyethers containing acrylic, fumaric or maleic functionality. The pigments used comprise inorganic pigments such as the titanium dioxide and the "Carbon Black", organic pigments on azo, phtalocyanine, anthraquinone etc. base.

The compounds (I) and (II) of the present invention act as photoinitiators and besides they may be used by themselves or in combination with other photoinitiators such as benzophenone, benzyldimethylketale, 2-hydroxypropylphenylketone, benzoin ethers etc. Particularly advantageous turns out the combination with tertiary amines which increase the cross-linking speed of the mixture, such as triethylamine, N-methyldiethanolamine, N,N-dimethylethanolamine, p-dimethylaminoethylbenzoate, in the way they are commonly used. For the pigmented systems turns out particularly advantageous the use of sensitizing substances or coinitiators, such as thioxanthones and their derivatives, in the way they are normally used.

In addition to the compounds having formula (I) and (II), many components may be included in the photopolymerizable system, such as thermal stabilizers, inhibitors of the thermal polymerization, sensitizers, photo-oxidations stabilizers such as steric hindrance amines, antioxidants, atmospheric oxygen exclusion agents, thermal generators of radicals such as organic and inorganic peroxides, peresters, hydroperoxides, benzopinacols, azoderivatives such as azobisisobutyronitrile, metallic compounds such as cobalt (II) salts, manganese, surface levelling agents, fillers, dyes, glass and carbon fibers, thixotropic agents. Other components are constituted by unphotopolymerizable polymers, present as chemically inert substances, such as nitrocellulose, polyacrylic esters, polyolefines etc., or cross-linkable polymers by alternative systems such as peroxides and atmospheric oxygen, or by acid catalysis or thermal activation, such as for instance polyisocyanates, urea, melamine or epoxy resins. Such photopolymerizable systems may be either of transparent kind or pigmented, and they are used in the printing, graphic arts, plastic meterials, metals, wood, glass etc. fields. Their use in the inks field, above all those having high pigmentation level must be particularly underlined: in this case the pigments are present in an amount ranging from 10 to 60% by weight, and preferably between 15 and 40%.

The compounds having formula (I) and (II) are generally used in a quantity between 0.01% and 20% by weight, and preferably between 0.5% and 5%; they show a great dispersibility in the photopolymerizable systems, to which they give a high photochemical reactivity and stability to light. The light sources used for the photopolymerization are high, medium or low-pressure mercury-vapor lamps or superactinic lamps, with emission bands in the region between 250 and 400 nm. Among the possible sources even the sunlight or other artificial sources, such as xenon, tungsten lamps and laser sources are included. In the cross-linking of the inks containing titanium dioxide, "doped" lamps with a particularly high emission between 350 and 450 nm are preferably used.

In the inks preparation, the above mentioned compositions are ground on a three cilinders refiner till a granulometry between 0.1 and 2 μm and preferably lower than 1 μm is achieved. Such grinding may be carried out either formerly or subsequently to the addition by simple agitation of a photoinitiator and coinitiator mixture, wherein the photoinitiator is contained in an amount between 30 and 70%. Finally the polymerization is obtained by known methods, by irradiation in the suitable wavelength range.

In the preparation of the photoinitiators above shown, having formula (I) and (II), the use of many methods known in literature is possible. The process of sulfonylation of the respective halogenoketones, by the reaction of the halogenoketon with the sodium salt of the 4-alkylphenyl-sulfinic acid has been found particularly suitable.

Generally the process consists of the following steps:

a) the arylsulfonyl chloride of formula (III) is made to react with sodium bicarbonate and sodium sulfite at a temperature between 50 and 90° C., in a polar solvent, to give the corresponding sodium arylsulfinate;

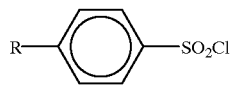

(III)

b) the dialkylbromoacetyl bromide of formula (IV) is made to react with the appropriate diphenyl sulfide of formula (V) (for the compounds (I) or with thianthrene (for compounds (II)), in presence of aluminum trichloride, in an organic solvent, at a temperature between 5 and 15° C., and the mixture is treated with mineral acids to give the corresponding 2-bromoketones for instance 4,4'-bis(2-bromo-2-methyl-1-propanoyl)-diphenyl sulfide (for the compounds (I)) or 2,6-bis(2-bromo-2-methyl-1-propanoyl)thianthrene (for the compounds (II));

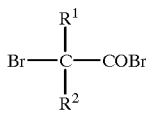

(IV)

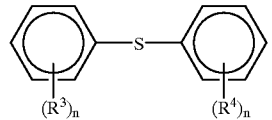

(V)

c) a mixture of sodium arylsufinate obtained in the step a) and the appropriate 2-bromoketone for instance 4,4'bis(2-bromo-2-methyl-1-propanoyl)-diphenyl sulfide (for the compounds (I)), or 2,2-bis(2-bromo-2-methyl-1-propanoyl) thianthrene, (for the compounds (II)), obtained by the step b), at a temperature between 80 and 120° C. in an organic solvent, is heated to give the final products (I) and (II).

The following examples of the present invention are reported for illustrative but not limitative aim:

EXAMPLE 1

Synthesis of the photoinitiator having formula (I): wherein n=0; R, $R^1$, $R^2$=$CH_3$; $R^3$, $R^4$=H:

4,4'-bis[2(4-methylphenylsulfonyl)-2-methyl-1-propanoyl]-diphenyl sulphide (Ia).

480 g of demineralized water, 106.6 g of sodium bicarbonate and 82.2 g of sodium sulfite are loaded in a 1 liter flask. The mixture is heated at 75° C. and 132.2 g of p-toluensulfonylchloride are loaded in 30'.

At the end of the addition the mass is kept at 80° C. for 30', then it is cooled at 25° C. and filtered: 101 g of sodium p-toluensulfinate are thus recovered after drying. Then the preparation of the 4,4'-bis(2-bromo-2-methyl-1-propanoyl)-diphenyl sulfide is started:

200 g of methylene chloride, 46.6 g of diphenyl sulfide and 116.8 g of 2-bromoisobutyryl bromide are loaded in a 500 ml flask. In one hour, keeping the temperature between 0° C. and 10° C., acting in an inert atmosphere, 70.0 g of aluminum trichloride are loaded.

At the end of the addition the mass is maintained under agitation for one hour at 15° C. The solution so obtained is poured in a mixture of hydrochloric acid at 30% (15 g), ice (188 g) and methylene chloride (40 g), maintaining the temperature between 15 and 20° C. The two phases are separated, the aqueous phase is extracted with 40 g of solvent and the reunited organic phases are washed with 50 g of demineralized water. The solvent is finally distilled, obtaining 117 g of 4,4'-bis(2-bromo-2-methyl-1-propanoyl)-diphenyl sulfide.

In the same reaction flask 365 g of n-butyl alcohol, 101 g of sodium p-toluensulfinate formerly prepared are added, and the whole is taken under reflux. It is left to reflux for 1 hour, it is cooled at 90° C. and a wash is done with demineralized water (60 g).

Then the waters are removed and the solution is cooled. 138 g of 4,4'-bis[2(4-methylphenylsulfonyl)-2-methyl-1-propanoyl]diphenyl sulfide are thus obtained after filtration of the product.

| $^1$H-NMR: | 1.7 ppm (12H, s) | aliphatic 4 $CH_3$ |
|---|---|---|
| | 2.5 ppm (6H, s) | on aromatic 2 $CH_3$ |
| | 7.35–8.0 ppm (16H, m) | aromatic 16 H |
| IR Spectrum: | ν (cm$^{-1}$) | Attribution |
| | 1670 | C=O |
| | 1590 | CH=CH |
| | 1300–1320 | $SO_2$ |
| | 1130–1150 | $SO_2$ |
| UV Spectrum ($CH_2Cl_2$; 5.66 mg/l): | | εmolar at 318 nm = 23550 |
| | | εmolar at 230 nm = 49340 |

Melting point=126° C.

TLC (on silica, eluant: petroleum ether/ethyl acetate=1/1): single spot at Rf 0.43.

EXAMPLE 1 bis

Synthesis of the photoinitiator having formula (I) wherein n=0; R, $R^1$=$CH_3$, $R^2$=$CH_2$—$CH_3$; $R^3$, $R_4$=0):

4,4'-bis[2(4-methylphenylsulfonyl)-2-methyl-1-butyryl]-diphenyl sulphide (Ib)

120 g of the above photoinitiator (Ib) are obtained by a process analogous to that followed in the example 1, by the use of 120 g of 2-bromo-2-methyl-butyryl bromide in alternative to 2-bromoisobutyrylbromide

| $^1$H-NMR: | 0.80 ppm (6H, t) | aliphatic 2$\underline{CH_3}$—$CH_2$ |
|---|---|---|
| | 1.70 ppm (6H, s) | aliphatic 2$\underline{CH_3}$—C |
| | 2.48 ppm (6H, s) | on aromatic 2$CH_3$ |

-continued

| | 2.40–2.54 ppm (4H, m) | aliphatic 2$\underline{CH_2}$—$CH_3$ |
| | 7.29–7.88 ppm (16H, m) | aromatic 16 H |
| IR Spectrum: | ν (cm$^{-1}$) | Attribution |
| | 1660 | C=O |
| | 1300 | $SO_2$ |
| | 1150 | $SO_2$ |
| UV Spectrum ($CH_2Cl_2$: 40 mg/l): | εmolar at 241 nm = 24395 | |
| | εmolar at 311 nm = 19187 | |

Melting point=about 60° C.

TLC (on silica, eluant: petroleum ether/ethylacetate=1/1): single spot at Rf=0.84.

EXAMPLE 2

Synthesis of the photoinitiator having formula (II $R^1=R^2=CH_3$):

2,6-bis [2(4-methylphenylsulfonyl)-2-methyl-1-propanoyl]-thianthrene (IIa).

140 g of the photoinitiator (IIa) are obtained by a process analogous to which followed in the example 1, using in spite of diphenyl sulfide 54 g of thianthrene.

| $^1$H-NMR: | 1.7 ppm (12H, s) | aliphatic 4 $CH_3$ |
| | 2.5 ppm (6H, s) | on aromatic 2 $CH_3$ |
| | 7.2–8.1 ppm (14H, m) | aromatic 14 H |
| IR Spectrum: | ν (cm$^{-1}$) | Attribution |
| | 1670 | C=O |
| | 1240–1310 | $SO_2$ |
| | 1150 | $SO_2$ |
| UV Spectrum ($CH_2Cl_2$; 10.2 mg/l): | εmolar at 250 nm = 35840 | |
| | εmolar at 265 nm = 29325 | |
| | εmolar at 325 nm = 5870 | |

Melting point=118° C.

TLC (on silica, eluant: petroleum ether/ethyl acetate=1/1):unitary spot at Rf=0.51.

The substances used in the following examples are commercialized with the following commercial denominations:

Ebecryl 600®, UCB (Belgium): linear epoxyacrylate oligomer.

Ebecryl 220®, UCB (Belgium): aromatic urethanoacrylate oligomer.

Trimethylolpropanetriacrylate: base trifunctional monomer.

Irgalite Blue BNSF®, CIBA: blue pigment.

Efka Polymer LP 8001®, EFKA CHEMICALS BV: polyacrylic base dispersant.

Verol 368®, LAMBERTI SpA: sulfosuccinic base wetting agent.

Speedcure EDB®, LAMBSON LTD (UK): coinitiator, 4-dimethylaminoethylbenzoate.

The comparison reported in the following examples has been carried out testing the following compounds:

betaketosulfonic derivative (Ia);

betaketosulfonic derivative (Ib);

betaketosulfonic derivative (IIa);

compound (III), corresponding to the 2-methyl-1-[4-(methylthio) phenyl]-2-(4-methylphenylsulfonyl) 1-propanone (contained in the American U.S. Pat. No. 5,026,740);

compound (IV), corresponding to the 2-methyl-1-[4-(methylthyo)phenyl]-2-morpholino-1-propanone (contained in the European Patent EP 88050) (MMMP).

EXAMPLE 3

| Composition of the matrix for the blue inks: | |
| --- | --- |
| reactive oligomers: (mixture of aromatic epoxy and urethane acrylates | |
| Ebecryl 600 ® | 43.0% |
| Ebecryl 220 ® | 11.5% |
| Reactive monomers: | |
| Trimethylolpropane triacrylate | 22.0% |
| Pigment: | |
| Irgalite Blue BNSF® | 22.0% |
| Additives: | |
| Efka Polymer LP 8001 ® | 0.6% |
| Verol 368 ® | 0.9% |

| Composition of the cross-linkable blue inks: | | | | | |
| --- | --- | --- | --- | --- | --- |
| | 1 | 2 | 3 | 4 | 5 |
| Matrix (%) | 92 | 92 | 92 | 92 | 92 |
| Compound (Ia) (%) | 4 | | | | |
| Compound (Ib) (%) | | | | | 4 |
| Compound (IIa) (%) | | 4 | | | |
| Compound (III) (%) | | | 4 | | |
| Compound (IV) (%) | | | | 4 | |
| Speedcure ED ® (%) | 4 | 4 | 4 | 4 | 4 |

Preparation of the inks: the compositions are grinded on a three cilinders refiner till a granulometry lower than one micron and photocross-linked by irradiation in the above reported conditions.

EXAMPLE 4

| Composition of the matrix for the white inks: | |
| --- | --- |
| reactive oligomers: (mixture of epoxy and urethanoaromatic acrylates). | |
| Ebecryl 600 ® | 26.6% |
| Ebecryl 220 ® | 7.1% |
| Reactive monomers: | |
| Trimethylolpropane triacrylate | 9.9% |
| Pigment: | |
| Titanium dioxide (rutile) | 55.5% |
| Additives: | |
| Efka Polymer LP 8001 ® | 0.35% |
| Verol 368 ® | 0.55% |

| Composition of the cross-linkable white inks: | | | | |
| --- | --- | --- | --- | --- |
| | 6 | 7 | 8 | 9 |
| Matrix (%) | 95 | 95 | 95 | 95 |
| Compound (Ia) (%) | 2.5 | | | |
| Compound (IIa) (%) | | 2.5 | | |
| Compound (III) (%) | | | 2.5 | |
| Compound (IV) (%) | | | | 2.5 |
| Speedcure EDB ® (%) | 2.5 | 2.5 | 2.5 | 2.5 |

Preparation of the inks, the compositions are grinded on a three cilinders refiner till a granulometry lower than one micron, and photocross-linked by irradiation in the above reported conditions. The characterization of the so obtained inks is carried out analysing the following parameters:

Reactivity determination

The ink is applied at a thickness of 1 micron, by a mechanical coater equipped with head for offset applications, on a PVC support and then it is passed at a distance of 15 cm from the light source, under the UV radiation of a 80 W/cm medium pressure mercury-vapor lamp, of which a Steinmann® photocross-linker is equipped. The greater is the line speed, the lower is the energy needed for the cross-linking, then the greater is the efficacy of the photoinitiator.

The cross-linking speed, measured in m/mim, is expressed as the maximum speed of the belt conveying the manufacture which allows the perfect ink cross-linking (tack free). The last is assured when, at the cross-linker outlet, the ink does not show superficial damagings after frictions with the edge of a folded sheet of paper or after repeated pressures and twists of the thumb well sticked on the surface (thumb twist test). In the above described conditions it is assumed that, if at the line velocity of 80 m/min the ink reaches the tack free conditions, it has a good applicative response.

Determination of the Post Curing Odour

The tested inks supported on PVC specimens, as above described for the reactivity determination, are passed under the indicated photocross-linker at a speed of 50 m/min to assure the complete polymerization and then the absence of odour due to the possible presence of unreacted acrylates, immediately ermetically and oven by one closed in jars and put in a thermostated oven at 60° C. After 1 hour a group of 5 persons gives an opinion on the residual odour produced by the inked specimens signed in an anonymous way. Then the persons give a qualitative opinion using a scale of empirical values between 1 and 5, where 1 means the minimum odour perception, and 5 means a strong perception.

Determination of the Yellow Index

In order to measure the yellow index, the only PVC specimens on which the white ink has been applied, immediately after the cross-linking, are put in the specimen holder of a BYK® calorimeter and the yellow index is measured according to the ASTM E 313 specification.

| RESULTS | | | | | |
|---|---|---|---|---|---|
| Blue Inks | 1 | 2 | 3 | 4 | 5 |
| Cross-linking velocity (m/min) | >80 | >80 | >80 | >80 | >80 |
| Post curing residual odour (average) | 1 | 2–3 | 3–4 | 5 | 1 |
| White Inks | 6 | 7 | 8 | 9 | |
| Cross-linking velocity (m/min) | >65 | >65 | >65 | >65 | |
| Post curing residual odour (average) | 1 | 2–3 | 3–4 | 5 | |
| Yellow Index | 7.5 | 7.7 | 7.6 | 7.5 | |

As it is possible to notice from the just reported data, the presence of the betaketosulphones (I) and (II) in the tested inks, in addition to assuring good applicative characteristics in terms either of line velocity or of yellow index, has the merit to give a scarce residual odour.

What is claimed is:

1. Photopolymerizable system containing at least a beta-ketosulphone selected from the compounds having formula (I) and (II):

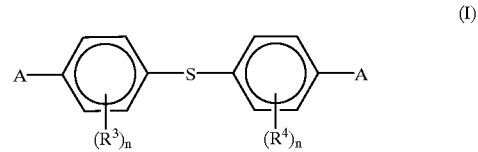

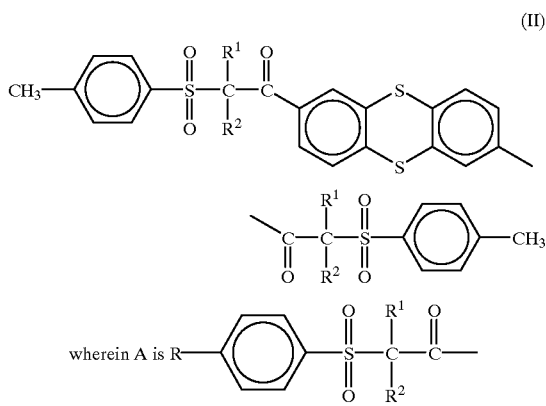

and R, $R^1$, $R^2$, $R^3$ and $R^4$ each independently are H or $C_{1-4}$ linear or branched alkyl chain and n is 0 or 1 in an amount ranging from 0.01 to 20% by weight.

2. Photopolymerizable system as claimed in claim 1, wherein said betaketosulphone is contained in an amount ranging from 0.5 and 5% by weight.

3. Pigmented ink containing at least a betaketosulphone selected from the compounds having formula (I) and (II):

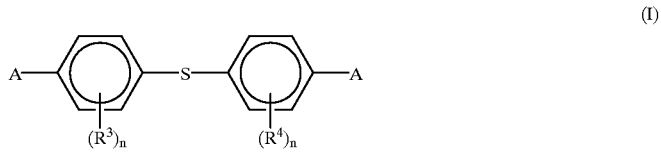

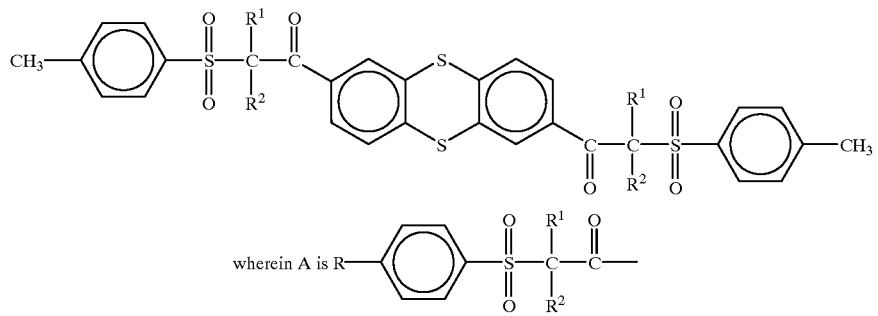

and R, $R^1$, $R^2$, $R^3$ and $R^4$ each independently are H or $C_{1-4}$ linear or branched alkyl chain and n is 0 or 1 in an amount ranging from 0.01 to 20% by weight.

4. Betaketosulphone derivative selected from the group consisting of (I) and (II):

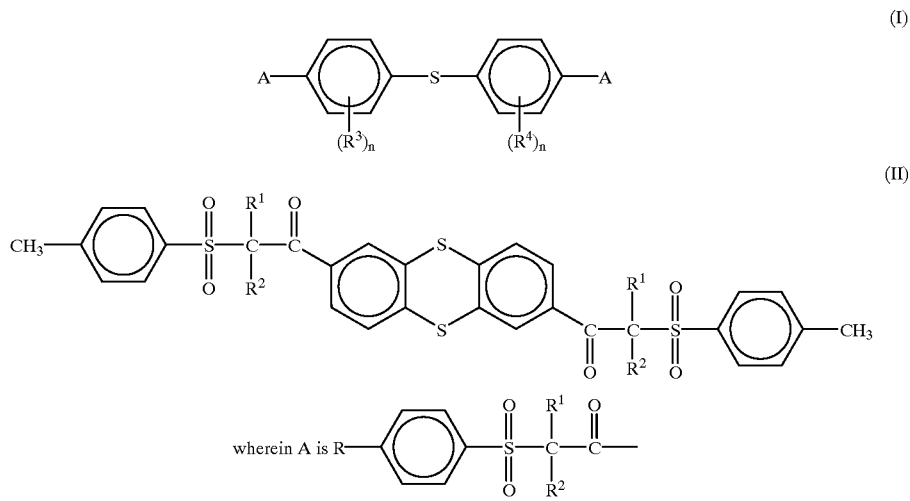

and R, $R^1$, $R^2$, $R^3$ and $R^4$ each independently are H or $C_{1-4}$ linear or branched alkyl chain and n is 0 or 1 suitable to the use as polymerization photoinitiator.

5. A method of photocuring a pigmented ink composition comprising at least one betaketosulphone selected from the group consisting of (I) and (II), as claimed in claim 4, as polymerization photoinitiator by exposing the composition to ultraviolet light.

* * * * *